United States Patent [19]
Stevens et al.

[11] Patent Number: 5,800,493
[45] Date of Patent: Sep. 1, 1998

[54] INTRAUTERINE ABLATION SYSTEM

[75] Inventors: Gail Stevens, Menlo Park; Todd A. Thompson, Sunnyvale; Steven A. Daniel, Fremont; Robert D. Warner, Cupertino, all of Calif.

[73] Assignee: Gynecare, Inc., Menlo Park, Calif.

[21] Appl. No.: 429,960

[22] Filed: Apr. 26, 1995

[51] Int. Cl.$^6$ .................................................. A61F 7/012
[52] U.S. Cl. ............................ 607/113; 607/105; 606/28
[58] Field of Search ......................... 606/20–23, 27–29, 606/119; 607/104, 105, 113, 114

[56] References Cited

U.S. PATENT DOCUMENTS

| | | |
|---|---|---|
| 1,259,344 | 3/1918 | Beardsley et al. |
| 2,074,634 | 3/1937 | Ackermann. |
| 2,077,453 | 4/1937 | Albright. |
| 2,088,586 | 8/1937 | Cole et al. ................................ 219/41 |
| 2,109,334 | 2/1938 | Kaden et al. ............................. 173/81 |
| 2,466,042 | 4/1949 | Reich et al. |
| 2,734,508 | 2/1956 | Kozinski. |
| 2,777,445 | 1/1957 | Hart. |
| 3,369,549 | 2/1968 | Armao. |
| 3,645,265 | 2/1972 | Majzlin. |
| 3,858,577 | 1/1975 | Bass et al. |

(List continued on next page.)

FOREIGN PATENT DOCUMENTS

| | | |
|---|---|---|
| 895 046 | 12/1953 | Germany. |
| 37 25 691 A1 | 3/1988 | Germany. |
| 1143149 | 2/1969 | United Kingdom. |
| WO 91/03996 | 4/1991 | WIPO. |
| WO 91/05528 | 5/1991 | WIPO. |
| WO 93/05737 | 4/1993 | WIPO. |
| WO 94/21202 | 9/1994 | WIPO. |
| WO 94/21203 | 9/1994 | WIPO. |
| WO 94/23794 | 10/1994 | WIPO. |
| WO 95/05869 | 3/1995 | WIPO. |
| WO 95/10326 | 4/1995 | WIPO. |

OTHER PUBLICATIONS

R.K. Gilchrist, "Potential Treatment of Cancer by Electromagnetic Heating", pp. 499–500, Apr. 1960, *Surgery, Gynocology & Obstetrics*.

F. Kristan Storm, William H. Harrison, Robert S. Elliott and Donald L. Morton, "Hyperthermic Therapy for Human Neoplasms", pp. 1849–1854, Oct. 15, 1980, *Cancer*.

Milton H. Goldrath, Terry A. Fuller and Shmuel Segal, "Laser Photovarporization of Endometrium for the Treatment of Menorrhagia", pp. 14–19, 1981, *Am. J. of Obstet. Gynecol.*

Charles Linke, Ahmad Elbadawi, Vernon Netto, Alan Roberts and Michael Russo, "Effect of Market Hyperthermia Upon the Canine Bladder", *Division of Urology and Department of Pathology, University of Rochester Medical School, Rochester, New York*.

*Primary Examiner*—John P. Lacyk
*Assistant Examiner*—Bryan K. Yarnell
*Attorney, Agent, or Firm*—Fulwider Patton Lee & Utecht, LLP

[57] ABSTRACT

An apparatus, and method for endometrial ablation by heating an inflation medium within a distensible bladder positioned within a uterus of a patient. The apparatus comprises an elongate tubular member, a handle, a distensible bladder and a heating element disposed within said distensible bladder. The system includes a controller configured for providing and regulating electric current to the heating element. The controller also includes a pressure sensor for regulating the pressure in the distensible bladder. Pressure and temperature displays and other operator controls are located on the controller unit. The method for performing endothelial ablation comprises inserting the distensible bladder and a portion of the tubular member into a uterus of a patient. The inflation medium within the distensible bladder is heated by providing electric current to the resistive wire of the heating element. The inflation medium within the distensible bladder is heated to a desired temperature and temperature and pressure within the distensible bladder are maintained for a desired time interval. The distensible bladder is then deflated and removed from the uterus.

2 Claims, 7 Drawing Sheets

U.S. PATENT DOCUMENTS

| | | | |
|---|---|---|---|
| 3,924,628 | 12/1975 | Droegemueller et al. | |
| 4,160,455 | 7/1979 | Law | |
| 4,315,512 | 2/1982 | Fogarty | |
| 4,461,923 | 7/1984 | Bogese, II | 174/36 |
| 4,709,698 | 12/1987 | Johnston et al. | |
| 4,754,752 | 7/1988 | Ginsburg et al. | |
| 4,799,479 | 1/1989 | Spears | |
| 4,949,718 | 8/1990 | Neuwirth et al. | 606/27 |
| 4,955,377 | 9/1990 | Lennox et al. | 606/27 |
| 5,004,472 | 4/1991 | Wallace | 606/194 |
| 5,045,056 | 9/1991 | Behl | 604/49 |
| 5,084,044 | 1/1992 | Quint | 606/27 |
| 5,084,060 | 1/1992 | Freund et al. | 606/192 |
| 5,087,256 | 2/1992 | Taylor et al. | 606/28 |
| 5,105,808 | 4/1992 | Neuwirth et al. | |
| 5,142,105 | 8/1992 | Kihlken et al. | 174/112 |
| 5,159,925 | 11/1992 | Neuwirth et al. | |
| 5,188,122 | 2/1993 | Phipps et al. | 128/788 |
| 5,190,540 | 3/1993 | Lee | 606/28 |
| 5,195,965 | 3/1993 | Shantha | 604/54 |
| 5,242,390 | 9/1993 | Goldrath | 604/55 |
| 5,257,977 | 11/1993 | Eshel | 604/113 |
| 5,277,201 | 1/1994 | Stern | 607/98 |
| 5,290,278 | 3/1994 | Anderson | 606/15 |
| 5,300,027 | 4/1994 | Foote et al. | 604/100 |
| 5,357,980 | 10/1994 | Seitzinger | 128/887 |
| 5,385,544 | 1/1995 | Edwards et al. | 607/101 |
| 5,403,309 | 4/1995 | Coleman et al. | 606/20 |
| 5,443,470 | 8/1995 | Stern et al. | 607/98 |
| 5,449,380 | 9/1995 | Chin | 606/28 |
| 5,460,628 | 10/1995 | Neuwirth et al. | 607/104 |

INTRAUTERINE ABLATION SYSTEM

BACKGROUND OF THE INVENTION

This invention relates to a system for ablation of the endometrium of a uterus of a patient, and more particularly to an intrauterine ablation system of the type having a heated distensible bladder secured to a tubular member connected to a controller for monitoring the pressure and regulating the temperature of an inflation medium.

The following terms as used herein have the meaning given below:

"Menorrhagia" means a condition causing excessive uterine bleeding in women.

"Cauterization" means the application of heat to tissue in an amount sufficient to destroy the tissue.

"Necrosis" means the death of cells in tissue.

"Endometrium" is that portion of the inner lining of the uterus to which an embryo normally attaches and excludes the portions of the uterine inner lining forming the cervix, to which the embryo usually does not attach.

Apparatus and methods for cauterization of the endometrium of a uterus, useful in sterilization procedures and cancer treatments, are well known. Thermal and cryogenic treatments have been utilized in such cauterization techniques and typically involve either the direct or indirect application of heat or cold to the tissue to be treated.

For example, a laser hysteroscope has been used to cauterize the endothelial layer of the uterus. Such a laser based procedure suffers from several disadvantages. Foremost, the use of a laser requires the application of an intense amount of thermal energy to a relatively small area of tissue, even though such a large amount of heat may not be necessary to effectively cauterize the tissue. Further, such a treatment requires the physician to continually reposition the laser used in the treatment within the uterus in order to treat the entire endometrium. Such internal manipulation of a laser hystero-scope within the uterus of a patient is both difficult, requiring a significant level of skill to perform, and potentially dangerous. Accidental puncture of the uterine or tissue wall may result from manipulation of the laser scope within the uterus or body cavity, and tissue layers beneath the endo-metrium may be burned if a laser's beam is left focused on one area of tissue for too long a period of time.

Methods and devices have been disclosed for necrosing tissue cells that utilize an extendable bladder which is inserted in the uterus and filled with a circulating fluid or gas at cryogenic temperatures. Such a bladder is maintained in substantially continuous contact with the inner surface of the uterine lining by using liquid nitrogen or freon to pressurize the bladder to a level which ensures adequate contact with the uterus. Such a method and apparatus suffers from the disadvantage of employing cryogenic fluids which could prove toxic to a patient in the event of bladder rupture. Another disadvantage is that the required extremely low temperatures pose a threat to tissue layers adjacent to the uterine endometrium.

A method is also known for effecting necrosis of the endometrium by inserting a distensible bladder into the uterus. The distensible bladder is inflated to a predetermined pressure with a fluid so that the distendable bladder is in contact with substantially all of the tissue lining for which necrosis is desired. The fluid is heated by means of a heating element positioned internal to said distendable bladder. The temperature and pressure of the fluid is controlled by means connected to the distendable bladder. The bladder is maintained inflated with the fluid at a temperature for a period of time sufficient to effect necrosis of the endometrium. Heretofore, such systems have been configured with inefficient heating elements and difficult to use catheters.

Consequently, there is a need for an intrauterine ablation system having a heating element disposed within a distensible bladder that is efficient, while providing reliable control of temperature and pressure, yet being economically and ergonomically configured.

SUMMARY OF THE INVENTION

Briefly and in general terms, the present invention provides an apparatus, system and method for endomthelrial ablation. The apparatus provides for heating of an inflation medium within a distensible bladder positioned within a uterus of a patient. The apparatus introduces the inflation medium under pressure into the distensible bladder so as to assure substantially uniform contact of the bladder with the endometrium. The system provides for regulating the temperature and pressure of the inflation medium while the distensible bladder is within the uterus for a desired period of time. The invention further provides a safe and efficacious method for ablating the endometrium of the uterus. The present invention thus provides a relatively inexpensive and easy method to treat menorrhagia in women.

The apparatus of the present invention comprises an elongate tubular member having a first lumen in fluid communication with a handle secured to the proximal end of the tubular member. The apparatus further includes a distensible bladder, for example, a latex rubber balloon, secured to the distal end of the tubular member, for example, a trilumen insertion catheter. A heating element is secured to the distal end of said elongate tubular member and disposed within said distensible bladder.

The heating element includes a tubular core member secured to the distal end of the elongate tubular member. A resistive wire is wound bifilar about the core member and a tubular heat conductive shell is disposed over the core member and the resistive wire. The shell is formed with a wall having a plurality of longitudinal slots for permitting the inflation medium to contact the resistive wire. A first thermocouple is secured to an outside surface of the wall of the tubular shell and a second thermocouple is secured to an inside surface of the wall of the tubular shell.

The handle body is secured to the proximal end of the elongate tubular member and is configured to be wye-shaped. The proximal end of the handle is configured with a fluid fill port connected to and in fluid communication with an inflation lumen of the tubular member. A valve is placed between and in fluid communication with the inflation lumen and the fill port. A syringe may be provided to connect with the fill port to inflate said distensible bladder with inflation medium to a desired pressure.

The wye of the handle further includes a pressure port in fluid communication with the inflation lumen. The one segment of the wye houses an electric socket connected to at least two wires carried within a second lumen of the tubular member and connected to the heating element. Similarly, the electric junction is connected to the four thermocouple leads carried by a third lumen of the tubular member.

The system for performing endothelrial ablation additionally comprises a controller configured to connect to the electrical socket for providing and regulating electric current to the heating element. The controller also includes a pressure sensor in fluid communication with the inflation lumen of the tubular member to provide a pressure signal to a pressure display for visualizing the pressure in the distensible bladder. Further, the controller includes a temperature converter for generating a temperature signal from the thermo-couples and a temperature display for visualizing the temperature within the distensible bladder. The pressure and temperature displays are located on a front panel of a box or unit which contains the controller components.

The controller further comprises a timer for generating an elapsed time signal which is connected to a display also on the front panel of the controller. A heating element controller is electrically connected to the heating element and configured to generate electric current to the resistive wire. Lastly, the controller includes a microprocessor configured to accept the pressure signal, the temperature signal and the elapsed time signal. The microprocessor is further configured to regulate the electric current generated by the heater controller as a function of the temperature, pressure and elapsed time.

The method of the present invention for performing endometrial ablation comprises providing a system in accordance with the present invention and inserting the distensible bladder and a portion of the tubular member into a uterus of a patient. A source of inflation medium is connected to the fluid fill port of the handle and the valve in the handle is opened. The distensible bladder is inflated with the inflation medium to a desired pressure and the valve is closed.

The inflation medium within the distensible bladder is heated by providing electric current to the resistive wire of the heating element. The method provides for heating the inflation medium within the distensible bladder to a desired temperature as indicated by the thermocouples and maintaining the temperature and pressure within the distensible bladder for a desired time interval. Afterwards, the distensible bladder is deflated and the distensible bladder and tubular member removed from the uterus of the patient.

These and other features and advantages of the present invention will become apparent from the following more detailed description, when taken in conjunction with the accompanying drawings which illustrate, by way of example, the principles of the invention.

DESCRIPTION OF THE PREFERRED EMBODIMENT

Figure 1:
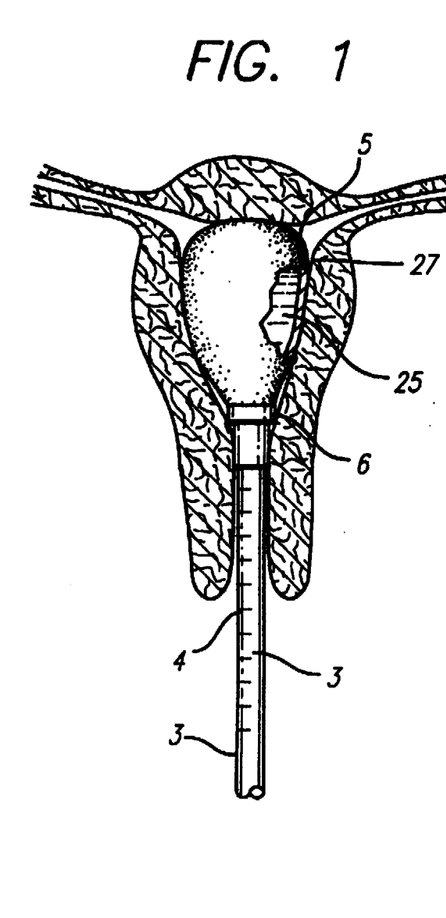
FIG. 1 depicts a distensible bladder utilized in the method of the present invention which has been inserted into and inflated within uterus of a patient.

FIG. 1 shows an inflated distensible bladder or balloon 5 attached to a trilumen insertion tubing 3 located within a human uterus 6. Inflation of the distensible bladder 5 with a fluid 25 assures uniform contact of the bladder with the endometrial tissue layer 27 of a uterus 6.

The trilumen insertion tubing 3 and the attached distensible bladder 5 must be sufficiently small, when the distensible bladder is deflated, so that it can be conveniently and safely inserted into the uterus 6 through a partially dilated cervix. The trilumen insertion tubing with the deflated bladder is aligned with the cervical canal after the cervix is exposed with a speculum and grasped with a tenaculum. After the distensible bladder 5 has been inserted, the distensible bladder 5 should be inflated to a pressure sufficient to ensure firm contact with the endometrial tissue layer on the interior uterine surface. The bladder pressure should be maintained at or about 45 to 200 mmHg, and preferably about 120 to 160 mmHg, to minimize risk of rupture of the distensible bladder 5 and possible internal injury to the patient.

The distensible bladder 5 must be capable of withstanding high temperatures without rupturing, and preferably is formed of a material that has good heat transfer characteristic to provide efficient heating action. A distensible bladder of a heat curing rubber, such as latex rubber has been found satisfactory. Inflation medium or fluid 25 preferably should be a sterile non-toxic fluid. A five percent dextrose in water solution has been found satisfactory.

Figure 2:
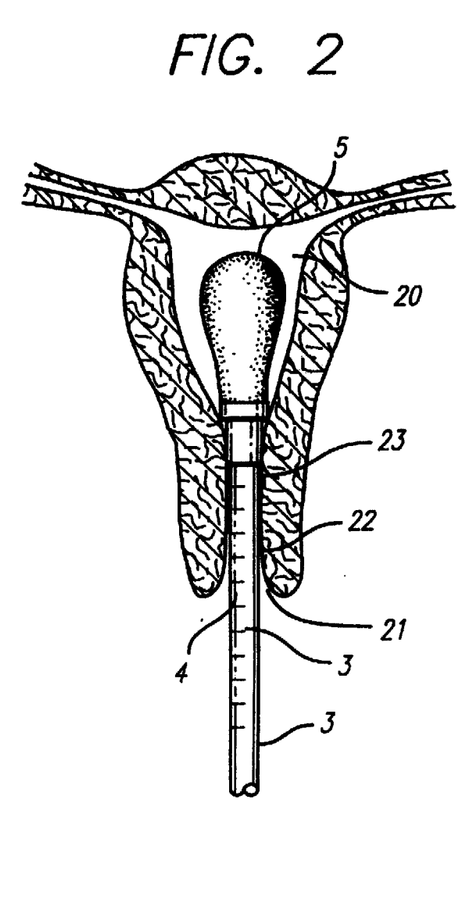
FIG. 2 depicts placement of the distensible bladder within the uterus.

As illustrated in FIG. 2, the uninflated distensible bladder 5 attached to trilumen insertion tubing 3 is inserted into the vagina 21, past the cervical os 22, through the cervical canal 23, for placement in the uterine cavity 20. Placement may be aided by virtue of scale gradations 4 present directly on the insertion tubing 3 to indicate the depth of insertion of the bladder 5. The trilumen insertion tubing 3 is made of semi-flexible material, for example acrylonitrile-butadiene-styrene (ABS), to permit easier insertion into the uterus, while providing support needed to manipulate the distensible bladder 5. The trilumen insertion tubing 3 is connected to a control unit 30 as shown in FIG. 3.

Figure 3:
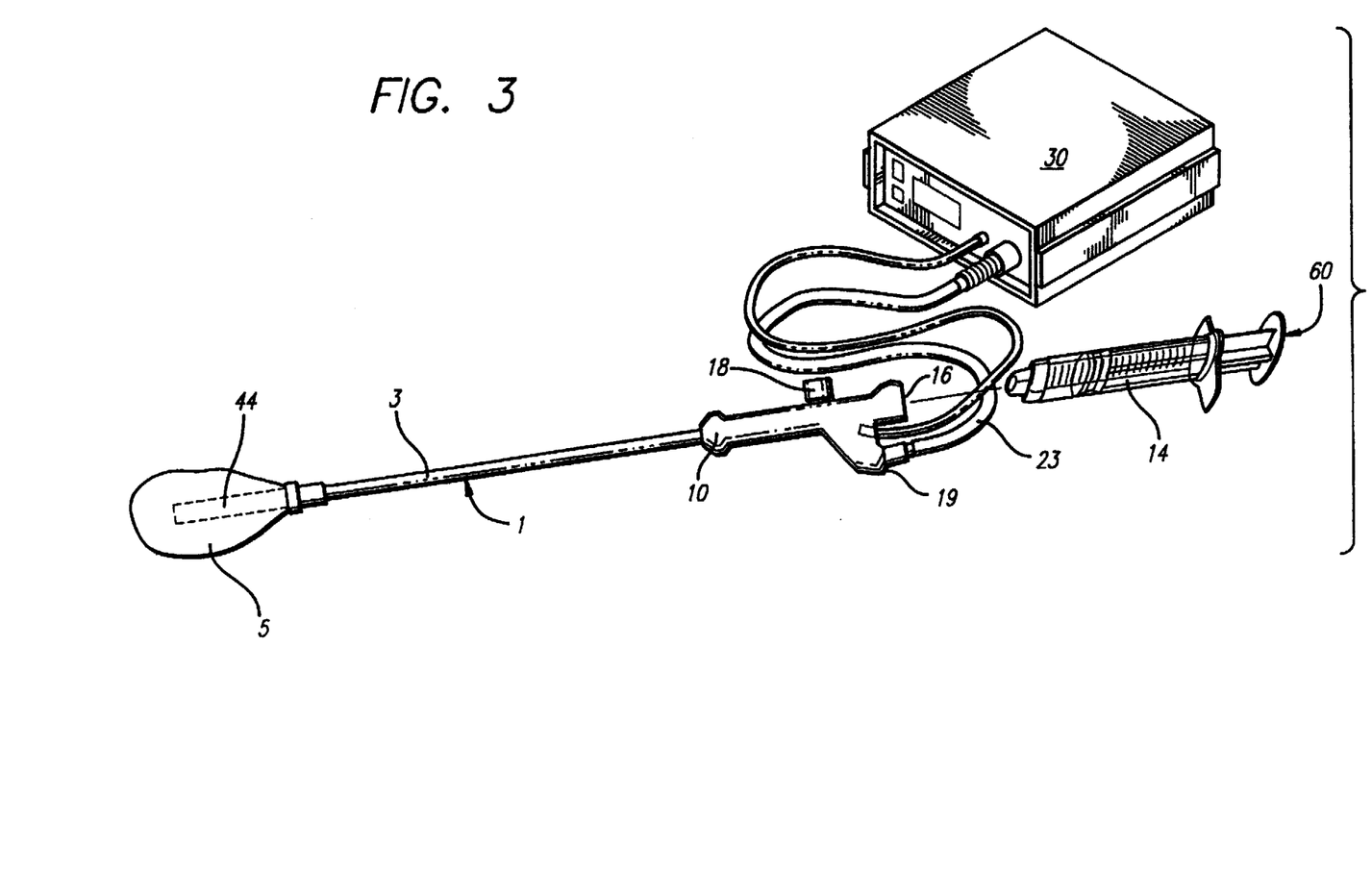
FIG. 3 is a perspective of an apparatus constructed in accordance with the invention that illustrates the balloon catheter connections.

FIG. 3 depicts the arrangement of control unit 30 and balloon catheter 1, comprising the distensible bladder 5, insertion tubing 3, catheter handle 10 and the interconnection of those elements. A fluid path comprises that portion of the invention through which the fluid 25 travels, including a fluid source such as a syringe 14, connected to the proximal end of catheter handle 10 via a fluid fill port 16, catheter handle 10, insertion tubing 3, and distensible bladder 5. Hypodermic barrel 14 is connected to the catheter handle 10 through fluid fill port 16 and may be secured in place by a luer lock or other suitable devices. A fluid fill valve 18 is also provided on the catheter handle 10. Manipulation of the fluid fill valve 18 enables the operator of the system to control the amount of fluid 25 in the fluid system, inflation and deflation of the distensible bladder by adding or removing fluid, respectively, and pressure of the fluid 25 in the system. Fluid fill valve 18 also provides protection for the patient by allowing fast and safe reduction of excessive pressures in the system that might build up through some malfunction.

Manipulation of the syringe 14, by depressing a plunger 60 and fluid fill valve 18 at the same time, causes inflation medium 25 to be introduced through the catheter handle 10 into the insertion tubing 3. The inflation medium 25 emerges from insertion tubing 3 and into distensible bladder 5, forcing distensible bladder 5 to expand into contact with the endometrial tissue layer 27 of the uterus 6. The fluid 25 is also directed along the flexible tubing 3 to the control unit 30 allowing measurement of the fluid pressure within the bladder as described below.

Each of the parts of the fluid path is in fluid communication providing constant fluid pressure within the entire fluid system and allowing measurement of pressure of the end attached to the control unit 30. Control unit 30 is connected to catheter handle 10 at its proximal end by means of an umbilical cord or cable 23.

Figure 7:
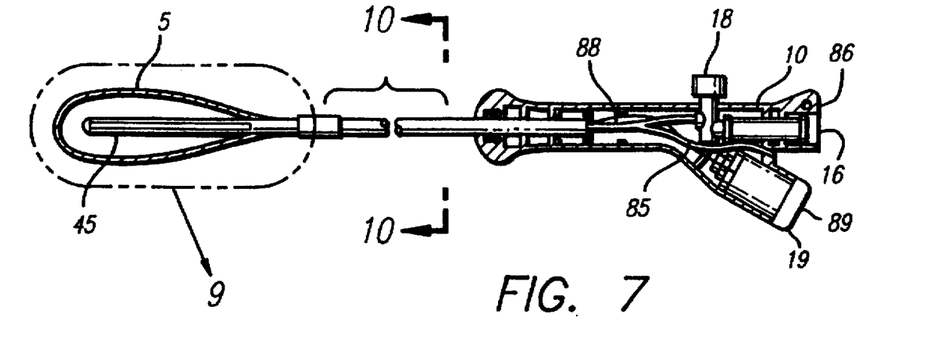
FIG. 7 is a cutaway view showing the catheter handle.
Figure 8:
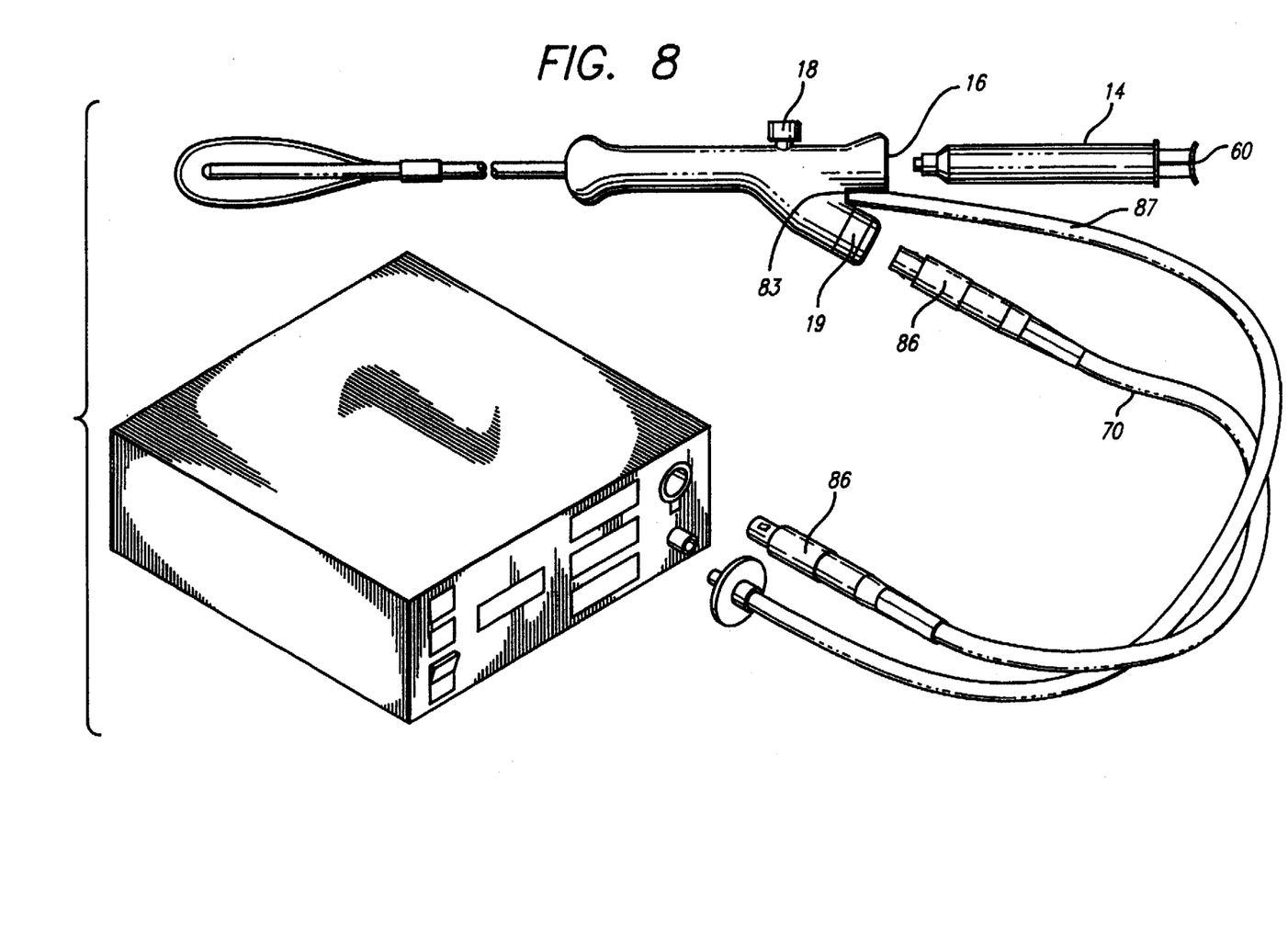
FIG. 8 is a side view of the handle and its connections to the control unit.

The catheter handle 11, shown in FIGS. 7 and 8 comprises a fluid fill valve 18, connection sacket 19 and connection part 83, and fluid fill port 16. Sacket 19 is designed to accept the power/temperature umbilical cable 70. As shown in FIG. 8, connection plugs 86 may be provided to secure the umbilical cable attachment to the catheter handle. Connection port 83 is designed to accept the pressure line 87.

When the syringe 14 is attached to fluid fill port 16 of the catheter handle 10, fluid can be introduced into the catheter by depressing the fluid fill valve 18 and the plunger 60 at the same time. The pressure display monitor located on the control unit 30 reads the pressure and if the pressure in the distendable bladder is below 70 or above 180 mmHg a warning signal and/or alarm alerts the user that the pressure is either too low or too high. A range of between 120 and 160 mmHg, preferably 150 mmHg is considered to provide the acceptable range of operation.

To remove excess fluid pressure from the distendable bladder 5 when the pressure is too high or when desiring complete removal of the catheter, the plunger 60 of the syringe 14 is drawn back while the fluid fill valve 18 is depressed to create and maintain a negative back pressure. This action will draw the distendable bladder 5 tighter against the catheter.

Referring now to FIG. 7, fluid fill valve controls the fluid pressure supplied to the distendable bladder by being internally connected to the internal pressure line 85 which is connected to the pressure line connector port 83. The body of the handle has a first extremity 86 and a second extremity 89 forming a wye. The fluid fill port 16 is disposed within the first extremity 86. The electrical connectors of the heating element 44 are disposed within the second extremity 89. A pressure port 83 for line 85 is also disposed between the first and second extremity 86 and 89. When fluid fill valve 18 and plunger 60 are depressed, the fluid will be supplied to the distendable bladder 5. Similarly, when the fluid fill valve 18 is depressed and the plunger 60 is drawn back, the resulting negative back pressure which forces the fluid away from the distendable bladder 5 and back into the insertion tube 3 to relieves the pressure.

Figure 4:
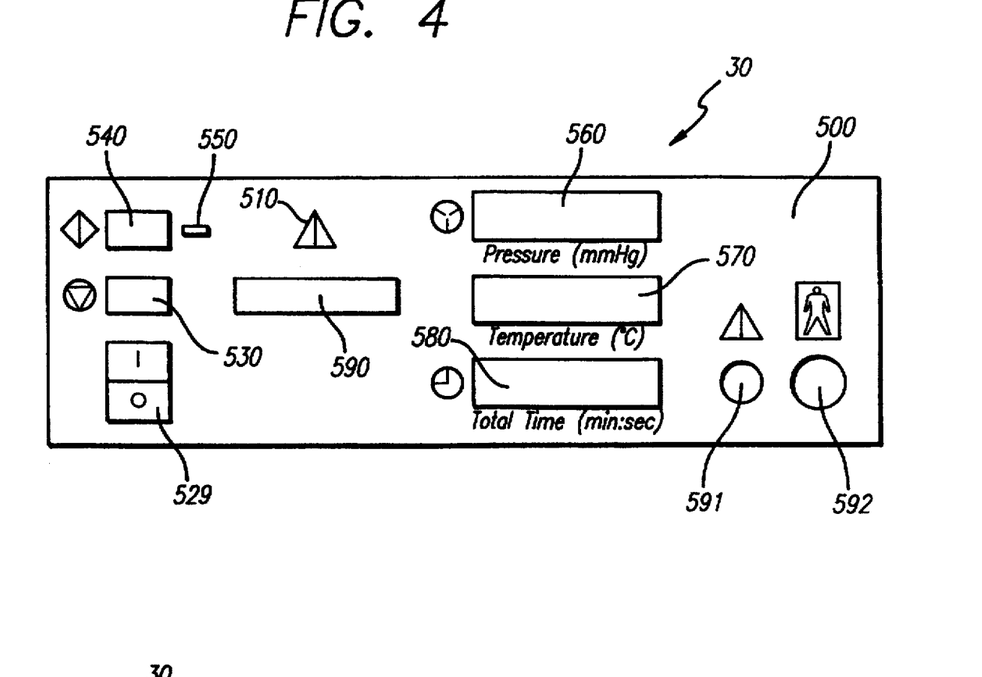
FIG. 4 depicts the front panel of the system control unit.

The control unit 30 is designed to regulate or control heat and operating times as well as monitor and display pressure valves. FIG. 4 shows the front panel 500 of control unit 30. The control unit 30 includes a power switch 529, start button 540 and start button light 550. The temperature of fluid 25 in the distensible bladder 5 is shown at catheter heater temperature display 570. Similarly, the pressure of the bladder is shown at display 560. These indicators allow the practitioner to readily reach the preset pressure range by varying the amount of fluid in the fluid path via manipulation of the syringe 14.

Fluid pressure within the bladder is monitored by displays located on the front of the control unit panel 500. The pressure connector 591 is designed for receiving the pressure line and is directly connected to the pressure transducer (not shown) internal to the control unit. The pressure transducer measures the internal pressure of the fluid path including the pressure of the fluid inside the distendable bladder. The pressure transducer generates a signal indicative of the internal pressure of the fluid path including the pressure inside the distensible bladder.

A connection port 592 is also provided for attaching the umbilical cable to the control unit which can be used both for providing cable and monitoring the temperature within the distendable bladder.

The control unit 30 is a software controlled system with necessary hardware safety backups. The software controls the fluid temperature and pressure, while monitoring the elapsed time of the procedure. The elapsed time is shown in minutes and seconds at display 580. The software includes steps like priming and filling the catheter and starting and stopping the heating therapy cycle. The temperature and pressure, however, are measured and read by both the hardware and the software.

Figure 12:
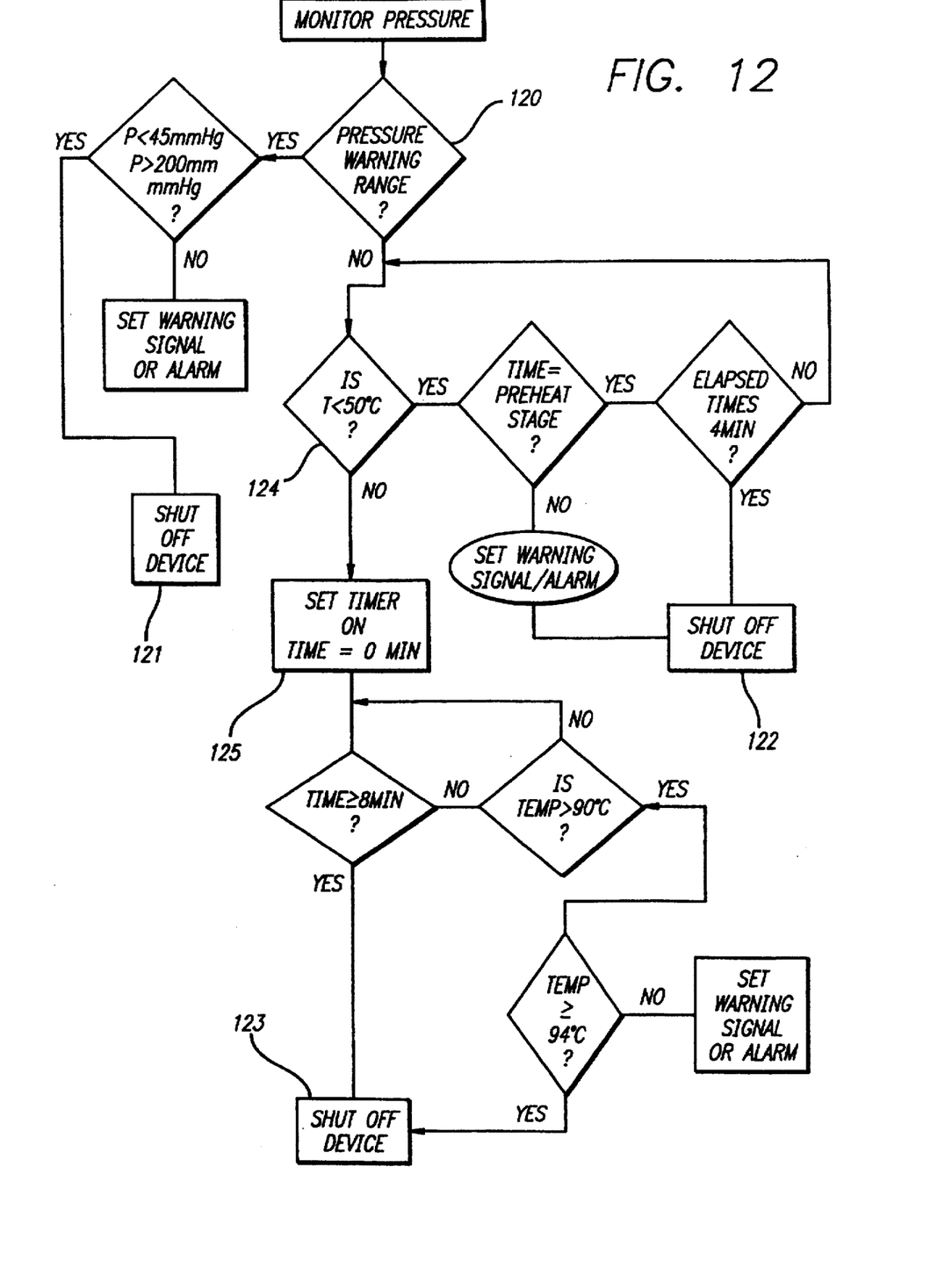
FIG. 12 is a flow chart of the process control loop showing the monitoring of temperature, pressure and time by the control unit.

FIG. 12 is a flow chart showing the monitoring of pressure, temperature and elapsed time by the control unit 30. Process control loop of FIG. 12 monitors the acceptable range of measurements for pressure, temperature and elapsed time. When the measurements for temperature, pressure and time exceed or fall below a certain point, the device automatically shuts off. However, before shut off range is reached, the device will alert the user that either pressure, temperature or time variable has entered a dangerously unacceptable range. The user can be alerted by either lighting the hazard light 510 on the control unit panel, by activating an alarm signal, or by both.

Step 121 shows that the present device shuts off automatically when the pressure either exceeds 200 mmHg or falls below 45 mmHg. Warning range 120 can be preset signifying that the pressure measurements are approaching a critical level. In one embodiment, for example, the user was alerted every time the pressure either exceeded 180 mmHg for 2 seconds, or fell below 70 mmHg for any time period.

Step 122 provides automatic shut off for time elapsed for preheat time. The preheat time, or the time it takes for the fluid temperature to reach the level where the therapy session is to be started is set here to a maximum of four minutes. If the temperature has not reached the therapy temperature, a warning signal is given and the device is shut off. Similarly, the elapsed time for the therapy session here is set to eight minutes, not including the preheat time, after which the device will automatically shut off as shown in step 123.

As shown in FIG. 12, the temperature is monitored and displayed by the software. It is desirable for the temperature to reach 85 to 90 degrees Celsius during therapy session, preferably 87 degrees Celsius. When the fluid 25 is first introduced, it has a temperature equal to room temperature. The heat from the body cavity can elevate this temperature to slightly above the room temperature at the onset of the procedure.

Step 124 shows the preheat stage, where the fluid temperature is raised from that of the room temperature to a temperature between 50 and 60 degrees Celsius, preferably 55 degrees Celsius. At 55 degrees Celsius, the therapy stage commences. The preheat stage 124 usually takes between thirty to ninety seconds but it can not exceed four minutes, since the device will automatically shut off operation after four minutes of preheat time if the temperature has not been elevated to 50 to 60 degrees Celsius.

During the therapy stage 125, the temperature is monitored regularly and the heating element 44 is controlled to either slow down the heating process or speed it up. In general both the speeding process during the initial preheat stage and the speeding up and slowing down process of the heating element 44 during the therapeutic stage is controlled by shutting on and off the heating element switch internal to control unit 30.

The software sets up special delays by which the amount of time that the heating element is on and off is controlled. For example, initially during the preheat stage, the heater may be on for 1 milli-second and off for 128 or 256 micro-seconds. But as the preheat stage is terminated and the therapy stage commences, the shut off time may be increased. Basically as shown in FIG. 12, during both the preheat and the therapy stage, the temperature gradient is monitored. If the temperature is increasing and approaching the upper temperature limit the ratio between the on time and off time, or the duty cycle time, is cut in half. Similarly, when the temperature is decreasing and reaching the lower limit, the on to off ratio is increased by a factor of two. This process is repeated until a change in achieved and the temperature either begins to rise or fall as desired. When the temperature enters the desirable range of 85 to 90 degrees Celsius, the duty cycle time is slowed down to maintain the desired range.

When the temperature exceeds 95 degrees or falls below 75 degrees Celsius at any time after the therapy session is started, the device will automatically terminate its operation. However, the user is first alerted before the heating element is shut off completely. In one embodiment, the user was alerted whenever the temperature exceeded 95 degrees or fell below 83 degrees Celsius for a period of 2 seconds or more. In this same embodiment, the heating element's operation would be automatically terminated whenever the temperature exceeded 90 degrees Celsius for 15 seconds (without having to exceed 95 degree limit).

The control unit hardware also includes error correction mechanism with error correction code embedded in the software. A communication port (not shown) or an output port for communication with I/O devices such as a PC printer can also be included when such need exists. The communication port includes a parity checker and interrupt handling mechanism.

In this manner, the control unit 30 monitors and displays instantaneous pressure and allows the device to operate between preset limits of 45 and 200 mmHg. If the pressure readings fall outside these limits, the hazard light 510 turns on.

Similarly, the unit also regulates the temperature inside the distensible bladder 5 by changing a series of electrical current pulses to the heating element 44. When the measured temperature exceeds a preset limit of about 95 degrees Celsius, the hazard light 510 turns on and the electrical current to the heating element is terminated and the user is instructed to abort the procedure.

Figure 5:
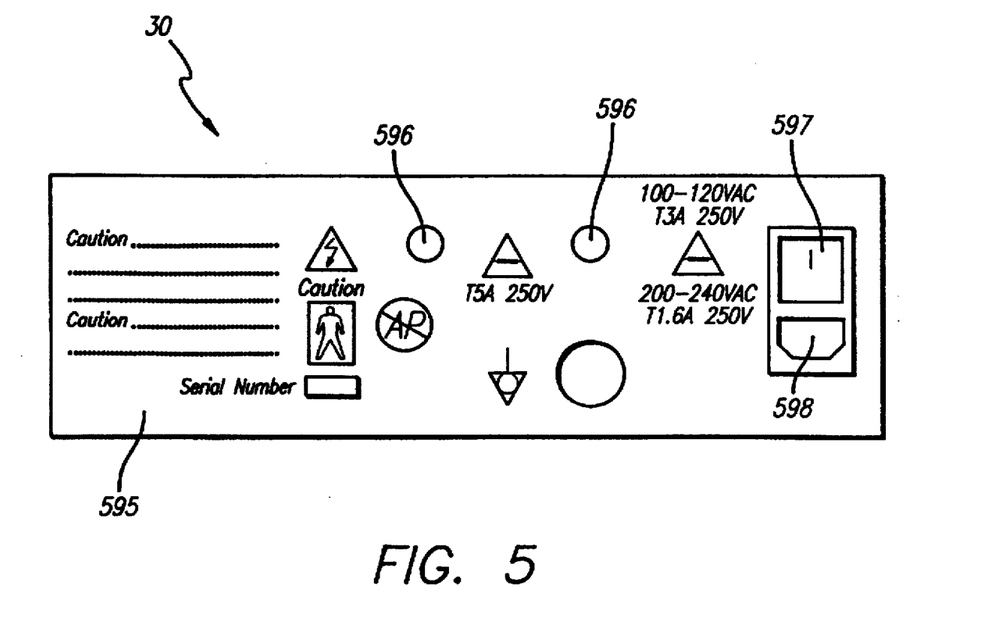
FIG. 5 depicts the rear panel of the system control unit.

FIG. 5 depicts the back end or rear of the control unit panel 595. Several fuses 596 are provided as well as a connection port 598 for the providing power to the unit. A voltage indicator 597 is also provided which can be adjusted so that the device is operable either at 110 or 220 V.

Figure 6:
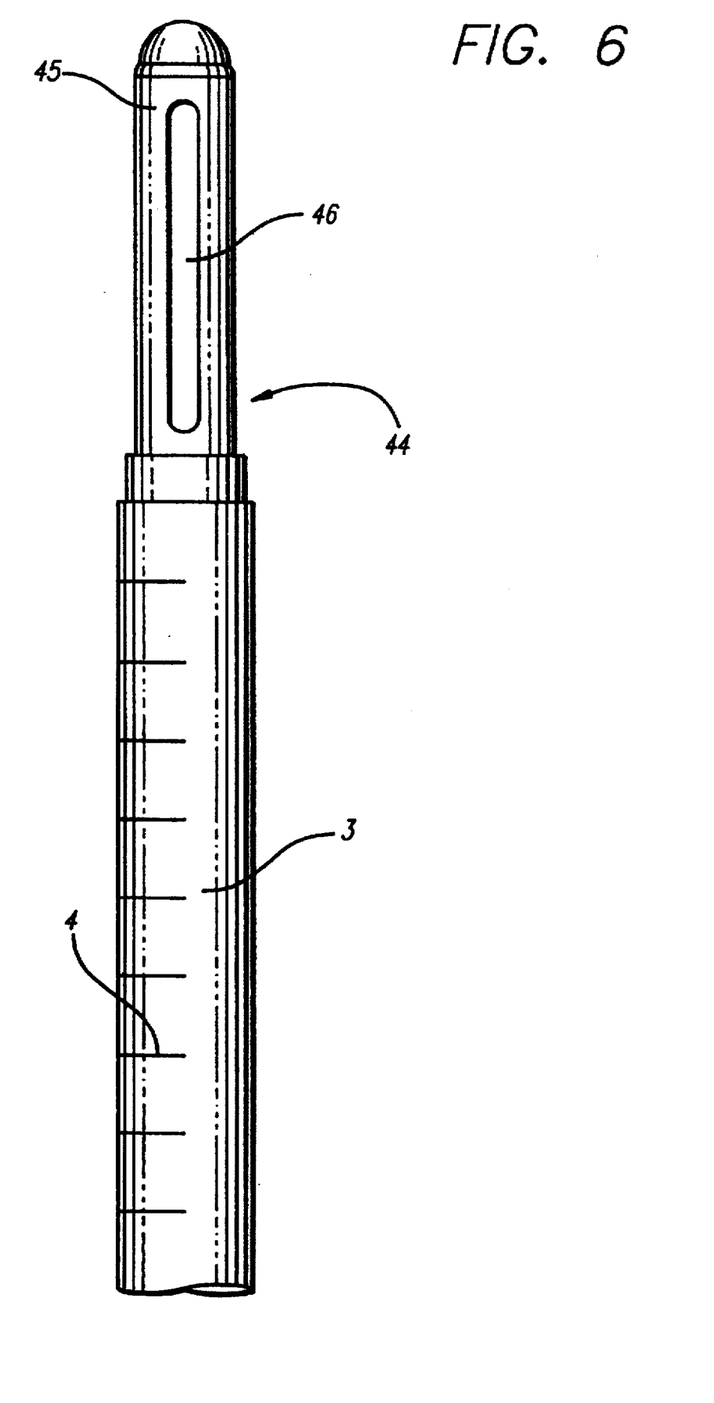
FIG. 6 is the vented heating element shell utilized in the method of the present invention.

Referring now to FIG. 6, at the distal end and affixed to the insertion tube 3, the distensible bladder 5 houses a heating element 44 and two thermocouples 66 and 68. The heating element 44 and one of the thermocouples 66 are surrounded by a heating element shell 45 which has circulation user 46, as shown in FIG. 6, to allow fluid inside the latex balloon to come in contact with the heating element and to protect the balloon from heater coils 47. The second thermocouple 68 is placed outside the heating element shield 45.

Figure 9:
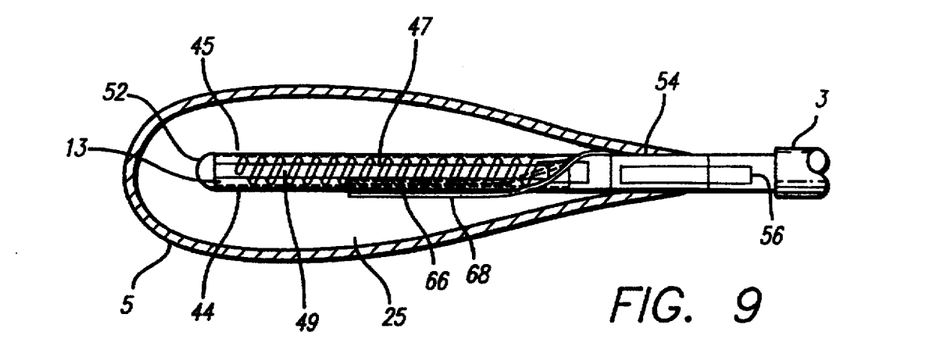
FIG. 9 is partial cross-sectional view showing the heating element of the embodiment shown in FIG. 7.

The heating element 44 can be viewed with reference to FIGS. 6 and 9. FIG. 6 is an external view of heating element 44, which comprises heating element shell 45 and circulation vents 46. FIG. 9 is a side view, more detailed depiction of the heating element 44, wherein resistive wire leads 49 provide power from system control unit 30 to heating element coil 47 causing heating element coil 47 to heat the fluid 25 which comes into contact with the heating element coil 47 as the fluid 25 flows through the circulation vents 46. The heating element coil 47 is a bifilar wound wire twisted around a core 49, the core being made preferably of ceramic material. The end of the looped wire is then affixed securely to the core 49 at each terminating end 13, and 21. Temperature of the fluid 25 is measured by thermocouple 48 and is displayed at temperature display 32. Heating element coil shell 45 prevents distensible bladder 5 from contacting the heating element coil 47 directly.

The distal end of the core and the heating shell are secured to a plastic tip 52 and the proximal end is secured to a second plastic housing 54 that contains the wires that carry the electrical current into the heating element. A structural support metal conduit 56 is partially embedded in this second plastic housing to ensure structural integrity. The second plastic body 54 is secured to the trilumen insertion tubing 3.

Figure 10:
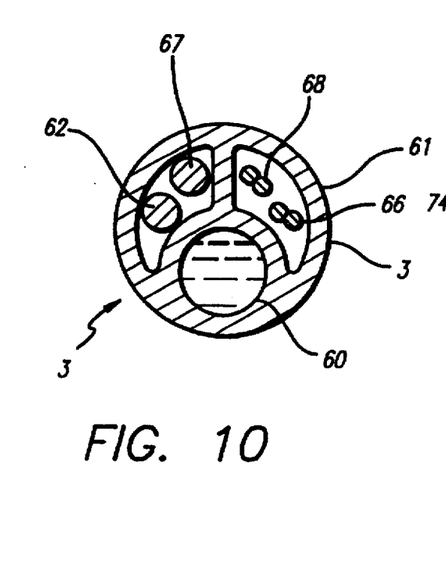
FIG. 10 is a cross-sectional view of the trilumen insertion tube showing the heating element wire leads and the thermocouple pairs.

FIG. 10 provides a cross-sectional view of the trilumen insertion tube 3. The trilumen insertion tube 3 has special internal pattern with a circular portion 60 in the middle and two pie shaped portions 61 and 62 encompassing the perimeter of the middle circular portion 60. The circular portion 60 is designed as a fluid channel or path into the distensible bladder 5. The two pie shaped portions 61 and 62 house the thermocouples 66 and 68 and the heater wires 67, respectively.

Figure 11:
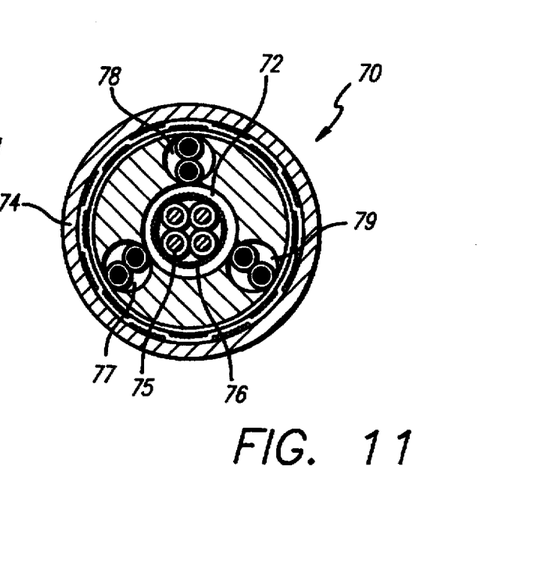
FIG. 11 is a cross-sectional view of the umbilical cable.

FIG. 11 depicts a cross-sectional view of the umbilical cable 70. The umbilical cable 70 is used to connect the control unit 30 to the balloon catheter 1, as shown in FIG. 3. The umbilical cable 70 conducts electrical power to the heating element 44, electrical temperature measurement signals from the thermocouples 75 and 76, and shields against Electro Magnetic Interference (EMI) and Radio Frequency Interference (RFI). The umbilical cable 70 interfaces with the control unit 30 and the balloon catheter 1 via a combination of dedicated electrical connectors like plugs and receptacles. The umbilical cable 70 is packed specifically to reduce the outside diameter of the cable.

FIG. 11 shows that the umbilical cable comprises a sheath 74 in which three sets of electrically conducted wires 77, 78 and 79 ultimately connected to the heating element 44 are twisted and packed within the sheath into a low profile twist.

An inner shield 72 is placed in the center of the cable 70. The inner shield 72 houses the two thermocouple pairs 75 and 76. The three sets of electrically conductive wires 77, 78 and 79 are placed at equidistant places around the perimeter of the inner thermocouple shield. These three sets of electrically conducted wires 77, 78 and 79 are ultimately twisted together to provide one set of heater wires which connect to the heating element 44.

The overall methodology used for this treatment of menorrhagia comprises of: powering on the controller; starting-up the initialization process; inserting and filling the catheter and pressurizing it to pressure set point; starting the heating therapy by activating the heating element; continuing the heat and pressure therapy for a preset time of about eight minutes; and monitoring the temperature and pressure during this time so that it does not go beyond a set point of about ninety degrees Celsius. At set time intervals, the current temperature is read to either increase until it reaches the set point, or to maintain the temperature after it reaches the set point.

The invention will now be illustrated by the following example.

EXAMPLE

The cauterization procedure is preceded by screening against cancer of the affected region within established norms. A PAP smear and endometrial biopsy/curettage must exclude cancer or precancerous lesions of the uterus and cervix. If a fibroid uterus is present, an ultrasound should exclude ovarian masses. The uterine cavity must be 10 cm or less in length to be suitable for the small distensible bladder size.

It would be preferable if the patient is in a post menstrual condition. Alternatively, the patient may be treated with Danazol or the equivalent. Danazol therapy causes reduction in bleeding to a rate of 800 ml daily as well as a thin endometrium. The treatment should be continued from the 5th day of the previous menstrual period until two weeks after the procedure. However, treating the patient with Danazol or requiring the patient to be in a post menstrual condition is not required. The patient will undergo the procedure in the ambulatory surgery unit or outpatient facility where Valium and/or Demerol can be given intravenously if there is pain during the heating phase of the procedure.

The applicator is inserted after a bimanual examination and speculum of the cervix. Dilation to 6 mm, may be required which may necessitate a local 1% lidocaine block of the cervix. Once in place, the applicator stem protrudes from the vagina and consists of an electrical connecting plug, pressure line, syringe fill port, and rigid tubing. Placement of the applicator may be facilitated by distance markings on the rigid tubing indicating depth of insertion.

Upon placement of the applicator, it will be connected to a control unit via attachment of the electrical connector and flexible tubing attached to the handle to their receptacles on the control unit.

Subsequent to insertion of the applicator, the control unit will be powered on. The temperature of the fluid in the bladder will be preset to 87 degrees Celsius by the control unit and can be measured via the thermocouple located within the bladder. Fluid pressure constraints are preset and upon inflation of the distensible bladder by introduction of fluid to the fluid system by depressing the plunger on the hypodermic barrel, can be easily measured by looking at the pressure display located on the control unit.

The practitioner then proceeds to inflate the distensible bladder by the plunger on the hypodermic barrel which may serve as the fluid source. The practitioner injects the fluid into the fluid system until the control unit display indicates that the fluid pressure is within the preset constraints. The volume required to fill the distensible bladder is about 30 cc in most cases in order to reach the pressure wherein the bladder is substantially in contact with all of the endometrium.

The practitioner then turns on the heating element in order to heat the fluid to a preset level. The heating element in the bladder is connected via the plug to bring the fluid in the bladder to a temperature of about 87 degrees Celsius. Once that temperature level is reached, the system timer is activated to time the procedure and provide automatic turn off of the heating element at the end of a pre-set period.

Upon completion of the procedure, the pressure valve and plunger are depressed to allow the fluid to be withdrawn from the fluid system causing the distensible bladder to deflate. Upon deflation of the distensible bladder, the applicator may be safely withdrawn from the patient.

What is claimed is:

1. An apparatus for endometrial ablation, the apparatus comprising;

an elongate tubular member having a proximal end, a distal end, a first lumen in fluid communication with the proximal end and the distal end, a second lumen extending between the proximal end and the distal end, and a third lumen extending between the proximal end and the distal end;

a distensible bladder secured to the distal end of said elongate tubular member and in fluid communication with the first lumen;

a heating element disposed within said distensible bladder and secured to the distal end of said elongate tubular member, said heating element having a plurality of electrically conductive wires disposed within the second lumen of said elongate tubular member, and said heating element having a pair of thermocouple wires disposed within the third lumen of said elongate tubular member; and a handle secured to the proximal end of said elongate tubular member including a body within which is disposed a fluid fill port connected to and in fluid communication with the first lumen of said elongate tubular member, a valve disposed between and in fluid communication with the first lumen of said tubular member and the fluid fill port, a pressure port in fluid communication with the first lumen of said tubular member, and an electrical connector in electrical communication with the plurality of electrically conductive and thermocouple wires disposed within the second and third lumens of said elongate tubular member, wherein the body of said handle has a distal end and a proximal end having a first extremity and a second extremity forming a wye, wherein the valve and fluid fill port are disposed within the first extremity, the electrical connector is disposed within the second extremity and the pressure port is disposed between the first extremity and the second extremity.

2. A method for performing endometrial ablation, the method comprising;

providing an apparatus as recited in claim 1;

inserting the distensible bladder and a portion of the tubular member into a uterus of a patient;

opening the valve in the handle;

introducing an inflation medium through the fluid fill port into the distensible bladder;

inflating the distensible bladder with the inflation medium;

closing the valve in the handle;

activating the heating element; and heating the inflation medium within the distensible bladder for a desired time interval.

* * * * *